United States Patent [19]

Jenck

[11] Patent Number: 4,508,917
[45] Date of Patent: Apr. 2, 1985

[54] PREPARATION OF ALKYL ADIPATES

[75] Inventor: Jean Jenck, Villeurbanne, France

[73] Assignee: Rhone-Poulenc Chimie de Base, Courbevoie, France

[21] Appl. No.: 479,937

[22] Filed: Mar. 29, 1983

[30] Foreign Application Priority Data

Apr. 7, 1982 [FR] France .................. 82 06225

[51] Int. Cl.$^3$ .............................. C07C 67/38
[52] U.S. Cl. .................. 560/204; 560/190; 560/193
[58] Field of Search ............... 560/204, 190, 193

[56] References Cited

U.S. PATENT DOCUMENTS 4,256,909 3/1981 Kummer et al. ............... 560/204
4,259,520 3/1981 Kummer et al. ............... 560/204
4,404,394 9/1983 Isogai et al. ............... 560/204

*Primary Examiner*—Natalie Trousof
*Assistant Examiner*—Vera C. Clarke
*Attorney, Agent, or Firm*—Burns, Doane, Swecker & Mathis

[57] ABSTRACT

Alkyl adipates are prepared by reacting an alcohol and carbon monoxide with an alkyl pentenoate in the presence of (i) a catalytically effective amount of a cobalt catalyst, (ii) a tertiary nitrogen base, and (iii) hydrogen, with the hydrogen comprising at least 0.1% by volume of the carbon monoxide, and said reaction being carried out in (iv) an aromatic hydrocarbon or substituted aromatic hydrocarbon reaction medium.

18 Claims, No Drawings

PREPARATION OF ALKYL ADIPATES

BACKGROUND OF THE INVENTION

1. Field of the Invention

The present invention relates to the preparation of alkyl adipates from alkyl pentenoates, and, more especially, to the selective preparation of alkyl adipates by reacting carbon monoxide and an alcohol with an alkyl pentenoate.

2. Description of the Prior Art

It is well known to this art [compare *Bulletin of the Chemical Society of Japan*, 46, pp. 526–527 (1973)] that a mixture containing dialkyl esters, and in particular an alkyl adipate, is obtained by reacting carbon monoxide and an alcohol with an alkyl pent-3-enoate, under high pressure and at elevated temperature, in the presence of cobalt carbonyl and an aromatic heterocyclic nitrogen base. However, the industrial-scale development of a technique of this type, the value of which is not contested in principle, is greatly jeopardized not only by the low efficacy of the catalyst system, but also by the substantial proportion of alkyl pentanoate formed, even though the reaction is carried out in the absence of hydrogen.

Furthermore, it too is well known to this art that the presence of small amounts of hydrogen in the reaction medium tends to increase the efficacy of cobalt-based catalysts in processes for the synthesis of esters by reacting an alcohol and carbon monoxide with an olefinic compound.

It has nevertheless also been found that, in the process in question, this favorable effect associated with the presence of small amounts of hydrogen is accompanied by an adverse influence on the selectivity of the process in respect of alkyl adipates, which are the specifically desired products.

In fact, it has been observed that the presence of hydrogen not only tends to increase the proportion of hydrogenation products in the reaction mixture, but is also capable of reducing the proportion of adipate in the diesters formed.

This adverse effect greatly detracts from the economics of the subject process, insofar as the utilization of the branched diesters and the alkyl pentanoates is uncertain or even nonexistent. In other words, the formation of these products, which are destroyed in practice, corresponds to an intolerable loss of starting material. Furthermore, hydrogen can be formed in situ from the traces of water which may be present in technical-grade reactants, according to the well known reaction:

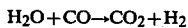

$H_2O + CO \rightarrow CO_2 + H_2$

It would be desirable, for obvious economic reasons, to be able to employ technical-grade carbon monoxide containing hydrogen, without this detracting from the selectivity of the process in respect of alkyl adipates, which are the desired diesters. It would also be desirable, for the same reasons, to be able to use reactants containing traces of water, without this resulting in a loss of starting material.

SUMMARY OF THE INVENTION

Accordingly, it has now surprisingly been found, and which is a major object of the present invention, that alkyl adipates are selectively prepared by reacting an alcohol and carbon monoxide with an alkyl pentenoate in the presence of a metal catalyst selected from the group comprising cobalt and its compounds, and in the further presence of a tertiary nitrogen base and hydrogen, the hydrogen representing at least 0.1% by volume of the carbon monoxide, provided that the reaction is carried out in an aromatic hydrocarbon which, if appropriate, can contain from 1 to 3 substituents independently selected from among alkyl, aryl and aralkyl radicals containing at most 20 carbon atoms.

DETAILED DESCRIPTION OF THE INVENTION

More particularly according to the present invention, an alcohol and carbon monoxide are therefore reacted with an alkyl pentenoate. Alkyl pentenoates can be obtained by reacting an alcohol and carbon monoxide with butadiene, in a manner which is in itself known. Alkyl pent-3-enoates are obtained as the principal products. Within the scope of the present process, it is also possible to use alkyl pent-2-enoates, which are obtained, for example, by isomerization of the corresponding pent-3-enoates, these α,β-unsaturated esters proving more reactive.

An alcohol is also used to carry out the present process. This other starting material can be represented by the formula R'OH, in which R' is an alkyl radical containing at most 12 carbon atoms and optionally substituted by one or two hydroxyl groups, or a cycloalkyl radical having from 5 to 7 carbon atoms, or an aralkyl radical having from 7 to 12 carbon atoms, or a phenyl radical.

Exemplary of alcohols which can be used according to the present invention, representative are methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol and phenol.

It is preferred to use an alkanol having at most 4 carbon atoms; methanol and ethanol are suitable for carrying out the present process. It is advantageous to use the alcohol corresponding to the alkyl radical of the pentenoate selected as the starting material.

The alcohol and the alkyl pentenoate can be used in stoichiometric amounts. However, it is preferable to use an excess of alcohol in a proportion of 1 to 10, or even more preferable to use from 2 to 5 mols of alcohol per mol of alkyl pentenoate.

The reaction is carried out in the presence of a metal catalyst selected from among cobalt and compounds thereof. Any source of cobalt which is capable of reacting with carbon monoxide in the reaction medium to give cobalt carbonyl complexes in situ can be used within the scope of the invention.

Examples of typical sources of cobalt are finely divided cobalt metal, inorganic salts, such as cobalt nitrate or carbonate, and organic salts, in particular carboxylates. Cobalt carbonyls or hydrocarbonyls can also be used; dicobalt octacarbonyl is suitable, for example, for carrying out the present process.

The molar ratio of the alkyl pentenoate to the cobalt generally ranges from 10 to 1,000. This ratio is advantageously set at a value ranging from 20 to 300.

The process according to the present invention also requires the presence of a tertiary nitrogen base having a $pK_a$ ranging from 3 to 10.

Preferably used are heterocyclic nitrogen compounds comprised of 5 to 6 ring members, which can contain one or two substituents selected from among alkyl or alkoxy groups having at most 4 carbon atoms, the hydroxyl group and halogen atoms, which optionally contain 2 or 3 double bonds and which can furthermore be fused to a benzene nucleus, if appropriate, provided that the ring members adjacent to the nitrogen heteroatom are neither substituted nor common to two rings.

6-Membered heterocyclic nitrogen compounds having a $pK_a$ of between 4 and 7, in particular pyridine, 4-picoline, isoquinoline and 3,5-lutidine, are more particularly preferred for carrying out the present process.

The amount of tertiary nitrogen base used is generally such that the molar ratio N/Co ranges from 1 to 50. To carry out the invention with especially good results, it is preferred that this ratio be set at a value ranging from 2 to 25.

One of the essential characteristics of the present process is the use, as a solvent, of an aromatic hydrocarbon which, if appropriate, can contain from 1 to 3 substituents independently selected from among alkyl, aryl and aralkyl radicals containing at most 20 carbon atoms.

More preferably, the solvents used can be represented by the formula:

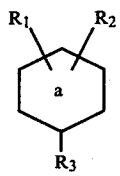

in which a is a benzene or naphthalene nucleus and $R_1$, $R_2$ and $R_3$, which are identical or different, represent hydrogen or an alkyl, aryl or aralkyl radical containing at most 20 carbon atoms. Preferably, at least one of the radicals $R_1$ to $R_3$ is a hydrogen atom and the other two radicals are selected from among hydrogen, alkyl radicals having at most 10 carbon atoms and the phenyl radical.

Preferably, a is a benzene nucleus, two of the radicals $R_1$ to $R_3$ represent a hydrogen atom and the third radical is an alkyl radical containing at most 4 carbon atoms or a phenyl radical.

Of course, it too is possible to use mixtures of several of these aromatic compounds, and in particular mixtures which are commonly available commercially.

Examples of solvents suitable for carrying out the present process are: benzene, naphthalene, toluene, ethylbenzene, cumene, tert.-butylbenzene, n-nonylbenzene, n-octadecylbenzene, methylnaphthalenes, isobutylnaphthalenes, diphenylmethane, biphenyl, xylenes, dimethylnaphthalenes, p-ethyltoluene, p-heptyltoluene, diethylbenzenes, methylisopropylbenzenes (cymenes), methylbiphenyls, 4,4'-dimethylbiphenyl, terphenyls, mesitylene and its isomers, ethylxylenes, trimethylnaphthalenes and the like.

Benzene and monoalkylbenzenes in which the alkyl radical contains at most 4 carbon atoms are the preferred, on the one hand because of the satisfactory results which they produce, and on the other hand because of their greater availability.

The amount of solvent, which influences the selectivity of the reaction, will generally be more than 20% (by weight) of the initial reaction mixture, and, to carry out the present process with good results, it will range from 30 to 60% (by weight) of the said mixture.

The process according to the present invention is also carried out in the presence of hydrogen, the hydrogen representing at least 0.1% (by volume) of the carbon monoxide.

To carry out the invention with good results, the hydrogen will represent at most 3% (by volume) of the carbon monoxide, and it will preferably represent from 0.5 to 2% (by volume) of the carbon monoxide.

Of course, although the hydrogen can be introduced into the reaction medium conveniently in the form of a mixture with the carbon monoxide, it can also be supplied separately.

The reaction is carried out in the liquid phase at a temperature above 120° C., there being no advantage in exceeding 200° C., under a carbon monoxide pressure which is at least 50 bars and can be as much as 1,000 bars. The reaction is preferably carried out at a temperature on the order of 130° to 180° C. and under a carbon monoxide pressure on the order of 100 to 300 bars.

In addition to hydrogen, the carbon monoxide used can contain impurities such as carbon dioxide, methane and nitrogen.

Upon completion of the reaction, or when the desired degree of conversion has been attained, the alkyl adipate is recovered by any suitable means, for example, by distillation or liquid-liquid extraction.

In order to further illustrate the present invention and the advantages thereof, the following specific examples are given, it being understood that same are intended only as illustrative and in nowise illustrative.

In said examples to follow, the following conventions are used:

The compounds resulting from the position isomerism of the olefinic double bond are not included in the products formed.

The products formed are essentially the diesters and the alkyl pentanoate, the latter resulting from the hydrogenation of the starting material ester.

A denotes the activity expressed in mols of products formed per hour and per gram atom of cobalt.

X(%) denotes the number of mols of diesters per 100 mols of products formed.

Y (%) denotes the number of mols of alkyl adipate per 100 mols of products formed.

Z (%) denotes the numbers of mols of alkyl pentanoate per 100 mols of products formed.

EXAMPLES 1 to 18

Control Experiments (a) to (j)

A series of experiments was carried out according to the following procedure:

Methyl pent-3-enoate (P3), methanol, dicobalt octacarbonyl (DCOC), isoquinoline and, if appropriate, a solvent were introduced into a 125 ml stainless steel autoclave purged under argon.

The autoclave was then purged with a stream of carbon monoxide, if appropriate containing hydrogen. The autoclave was then heated to the temperature T under a pressure P. After a reaction period (designated by t and expressed in hours) at this temperture, the autoclave was cooled and degassed. The reaction mixture was analyzed by gas chromatography. The particular conditions and also the results obtained are respectively reported in Tables (A) and (B) below:

In Table A, the ratios MeOH/P3, P3/Co and N/Co denote, respectively, the molar ratio of the methanol to the pent-3-enoate (Example 12 was carried out starting from methyl pent-2enoate), the ratio of the number of mols of pent-3-enoate to the number of gram atoms of cobalt, and the ratio of the number of mols of isoquinoline to the number of gram atoms of cobalt.

Control experiments (a) to (d) clearly show that, in the absence of solvent, the presence of hydrogen results in an increase in the efficiency of the cobalt-based catalyst and in a substantial drop in selectivity with respect to dimethyl adipate.

Control experiment (e) shows that, in the absence of hydrogen, the presence of benzene in the reaction medium made it possible to obtain dimethyl adipate with a noteworthy selectivity. However, the efficacy of the cobalt-based catalyst was very low under these conditions. Examples 1 to 4 show that the simultaneous presence of benzene and hydrogen made it possible to obtain dimethyl adipate selectively and efficiently.

TABLE (A)

| Ref. | P3 mmol. | MeOH mmol. | DCOC mmol. | MeOH/P3 | P3/Co | N/Co | H$_2$ (% by volume) | P bars | T °C. |
|---|---|---|---|---|---|---|---|---|---|
| a | 50.1 | 109 | 0.96 | 2.17 | 24.6 | 4 | 0 | 130 | 160 |
| b | 49.7 | 99 | 0.88 | 1.99 | 28.5 | 4.5 | 0.7 | " | " |
| c | 99.8 | 198 | 2.00 | 1.98 | 25.0 | 12 | 0.9 | " | " |
| d | " | 200 | 2.01 | 2.00 | 24.8 | " | 2.6 | " | " |
| e | 50.8 | 43 | 1.01 | 0.85 | 25.1 | 3.9 | 0 | " | " |
| 1 | 50.2 | 40 | 1.00 | 0.80 | " | 4.0 | 0.8 | " | " |
| 2 | 50.1 | 41 | 1.03 | 0.82 | 24.4 | 4.0 | 2 | " | " |
| 3 | 50.6 | 102 | 1.00 | 2.01 | 25.3 | 11.9 | 0.8 | " | " |
| 4 | 50.3 | " | 0.95 | 2.03 | 26.4 | 12.6 | 2 | " | " |
| f | 50.3 | 104 | 1.00 | 2.06 | 25.2 | 3.9 | 0.8 | " | " |
| 5 | 49.9 | 100 | 0.99 | 2.00 | 25.1 | 3.9 | " | " | " |
| 6 | 49.2 | 101 | 0.92 | 2.05 | 27.3 | 4.3 | " | " | " |
| 7 | 50.2 | 100 | 0.98 | 1.99 | 25.7 | 4.2 | " | " | " |
| 8 | 48.8 | 100 | 0.97 | 2.05 | 25.7 | 4.1 | " | " | " |
| g | 100 | 198 | 2.00 | 1.98 | 24.9 | 2.1 | " | " | " |
| 9 | 50.1 | 102 | 1.01 | 2.03 | 24.7 | 2.0 | " | " | " |
| h | 101 | 196 | 1.97 | 1.94 | 25.6 | 8.1 | " | " | " |
| 10 | 50.4 | 97 | 0.94 | 1.92 | 26.7 | 8.4 | " | " | " |
| i | 49.6 | 104 | 0.98 | 2.09 | 25.0 | 20.6 | " | " | " |
| 11 | 50.1 | 101 | 1.02 | 2.01 | 24.6 | 19.5 | " | " | " |
| 12 | 50.2 | 100 | 1.02 | 1.99 | 25 | 3.9 | 0.7 | " | " |
| 13 | 50.2 | 102 | 1.90 | 2.03 | 13.2 | 4.2 | 0.8 | " | " |
| 14 | 99.9 | 201 | 1.03 | 2.01 | 48.5 | 7.9 | " | 250 | 180 |
| 15 | 100 | 102 | 1.00 | 1.02 | 50.1 | 7.9 | " | " | " |
| j | 49.7 | 98,4 | 1.01 | 1.98 | 24.5 | 7.9 | " | 130 | " |
| 16 | 50.0 | 99,0 | 1.02 | " | 24.4 | 7.9 | " | " | " |
| 17 | 50.2 | 102 | 1.01 | 2.03 | 24.8 | 3.9 | 1 | " | 160 |
| 18 | 49.7 | 99 | 1.02 | 1.99 | 24.4 | 3.8 | " | " | " |

TABLE (B)

| Ref. | SOLVENT nature | (% by weight) | t | A | X (%) | Y (%) | Z (%) |
|---|---|---|---|---|---|---|---|
| a | — | 0 | 1 | 3.7 | 95.1 | 79.4 | 4.9 |
| b | — | 0 | " | 10.4 | 89.0 | 74.6 | 10.4 |
| c | — | 0 | " | 1.9 | 94.7 | 75.5 | 4.9 |
| d | — | 0 | " | 3.3 | 92.5 | 74.7 | 6.8 |
| e | benzene | 51 | 2 | 1.2 | 97.3 | 83.5 | 2.7 |
| 1 | " | " | " | 4.6 | 97.0 | 83.7 | 2.1 |
| 2 | " | " | " | 5.3 | 92.4 | 79.6 | 6.7 |
| 3 | " | 41 | " | 5.2 | 94.7 | 80.0 | 5.0 |
| 4 | " | 42 | " | 5.0 | 93.8 | 79.3 | 5.6 |
| f | — | 0 | " | 7.9 | 92.3 | 76.4 | 7.0 |
| 5 | benzene | 20 | " | 6.9 | 92.5 | 77.6 | 6.4 |
| 6 | " | 46 | " | 4.5 | 95.2 | 82.4 | 4.2 |
| 7 | toluene | 46 | " | 2.9 | 95.3 | 81.9 | 4.1 |
| 8 | t-butylbenzene | 47 | " | 3.4 | 95.1 | 81.7 | 4.1 |
| g | — | 0 | " | 5.6 | 94.8 | 78.2 | 4.5 |
| 9 | benzene | 48 | " | 2.1 | 94.1 | 80.0 | 4.4 |
| h | — | 0 | " | 2.4 | 94.9 | 76.6 | 4.6 |
| 10 | benzene | 44 | " | 5.3 | 95.1 | 80.5 | 4.0 |
| i | — | 0 | " | 1.1 | 90.1 | 73.7 | 8.8 |
| 11 | benzene | 38 | " | 3.9 | 94.5 | 77,2 | 5.2 |
| 12 | " | 46 | " | 7.6 | 95.3 | 81.6 | 4.2 |
| 13 | " | 60 | " | 2.6 | 95.2 | 81.7 | 4.2 |
| 14 | " | 31 | " | 13.9 | 95.1 | 80.8 | 4.4 |

TABLE (B)-continued

| Ref. | SOLVENT nature | (% by weight) | t | A | X (%) | Y (%) | Z (%) |
|---|---|---|---|---|---|---|---|
| 15 | " | 52 | " | 5.4 | 95.5 | 78.3 | 3.9 |
| j | — | 0 | " | 5.6 | 88.0 | 74.8 | 11.6 |
| 16 | benzene | 44 | " | 7.4 | 91.6 | 79.3 | 8.1 |
| 17 | naphthalene | 50 | " | 4.6 | 96.3 | 82.4 | 3.7 |
| 18 | biphenyl | 50 | " | 5.4 | 95.0 | 81.3 | 4.3 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an alkyl adipate, comprising reacting an alcohol and carbon monoxide with an alkyl pentenoate in the presence of (i) a catalytically effective amount of a cobalt catalyst, (ii) a tertiary nitrogen base, and (iii) hydrogen, with the hydrogen comprising at least 0.1% by volume of the carbon monoxide, and said reaction being carried out in (iv) an aromatic hydrocarbon or an alkyl, aryl or aralkyl substituted aromatic hydrocarbon reaction medium.

2. The process as defined by claim 1, said aromatic hydrocarbon (iv) bearing from 1 to 3 substituents, each being an alkyl, aryl or aralkyl radical having up to 20 carbon atoms.

3. The process as defined by claim 1, said aromatic hydrocarbon (iv) having the formula:

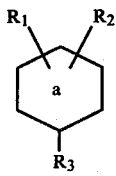

in which a is a benzene or naphthalene nucleus and $R_1$, $R_2$ and $R_3$, which may be identical or different, each represents hydrogen or an alkyl, aryl or aralkyl radical having up to 20 carbon atoms.

4. The process as defined by claim 3, wherein at least one of the radicals $R_1$ to $R_3$ is a hydrogen atom and the other two radicals are independently hydrogen, an alkyl radical having up to 10 carbon atoms or a phenyl radical.

5. The process as defined by claim 3, wherein a is a benzene nucleus.

6. The process as defined by claim 3, wherein the aromatic hydrocarbon (iv) is benzene or a monoalkylbenzene in which the alkyl radical contains up to 4 carbon atoms.

7. The process as defined by claim 1, wherein the aromatic hydrocarbon (iv) comprises at least 20% by weight of the initial reaction mixture.

8. The process as defined by claim 7, wherein the aromatic hydrocarbon (iv) comprises from 30 to 60% by weight of the initial reaction mixture.

9. The process as defined by claim 7, wherein the hydrogen (iii) comprises at most 3% by volume of the carbon monoxide.

10. The process as defined by claim 9, wherein the atomic ratio N/Co ranges from 1 to 50.

11. The process as defined by claim 10, wherein the reaction temperature ranges from 120° to 200° C.

12. The process as defined by claim 11, wherein the reaction pressure ranges from 50 to 1,000 bars.

13. The process as defined by claim 10, said atomic ratio N/Co ranging from 2 to 25.

14. The process as defined by claim 11, said reaction temperature ranging from 130° to 180° C.

15. The process as defined by claim 12, said reaction pressure ranging from 100 to 300 bars.

16. The process as defined by claim 3, said tertiary nitrogen base (ii) having a $pK_a$ ranging from 3 to 10.

17. The process as defined by claim 16, said tertiary nitrogen base (ii) having a $pK_a$ ranging from 4 to 7.

18. The process as defined by claim 16, said reactant alcohol comprising methanol, ethanol, isopropanol, n-propanol, tert.-butanol, n-hexanol, cyclohexanol, 2-ethylhexan-1-ol, dodecan-1-ol, ethylene glycol, hexane-1,6-diol, benzyl alcohol, phenylethyl alcohol or phenol.

* * * * *